US005921995A

United States Patent [19]

Kleshinski

[11] Patent Number: 5,921,995

[45] **Date of Patent: *Jul. 13, 1999**

[54] ANASTOMOSIS DEVICE

[75] Inventor: Stephen J. Kleshinski, Scituate, Mass.

[73] Assignee: Nitinol Medical Technologies, Inc., Boston, Mass.

[ * ] Notice: This patent is subject to a terminal disclaimer.

[21] Appl. No.: 08/984,193

[22] Filed: Dec. 3, 1997

Related U.S. Application Data

[62] Division of application No. 08/733,139, Oct. 16, 1996, Pat. No. 5,755,778.

[51] Int. Cl.⁶ .............................. A61B 17/08; A61F 2/06

[52] U.S. Cl. ................................ 606/153; 623/1; 623/12

[58] Field of Search ........................... 623/1, 12; 606/153

[56] References Cited

U.S. PATENT DOCUMENTS

| | | | |
|---|---|---|---|
| 5,100,429 | 3/1992 | Sinofsky et al. | 606/195 |
| 5,354,308 | 10/1994 | Simon et al. . | |
| 5,360,443 | 11/1994 | Barone et al. | 623/1 |
| 5,395,390 | 3/1995 | Simon et al. . | |
| 5,405,377 | 4/1995 | Cragg . | |
| 5,443,497 | 8/1995 | Venbrux . | |
| 5,456,712 | 10/1995 | Maginot . | |
| 5,514,176 | 5/1996 | Bosley, Jr. . | |
| 5,522,881 | 6/1996 | Lentz | 623/1 |
| 5,540,712 | 7/1996 | Kleshinski et al. | 623/1 |
| 5,617,878 | 4/1997 | Taheri | 623/1 |
| 5,720,776 | 2/1998 | Chuter et al. | 623/1 |
| 5,725,549 | 3/1998 | Lam | 623/1 |
| 5,755,772 | 5/1998 | Evans et al. | 623/1 |
| 5,755,778 | 5/1998 | Kleshinski | 623/1 |

*Primary Examiner*—Paul B. Prebilic
*Attorney, Agent, or Firm*—Sixbey, Friedman, Leedom & Ferguson; Daniel W. Sixbey

[57] ABSTRACT

A unitary anastomosis device for use in forming a graft between two body members is provided which includes a body member of fluid impervious vessel compatible material formed to define at least one elongate chamber having at least two spaced open ends. The outer surface of the body member carries a bio-adhesive which bonds the body member to the luminal walls of two vessels to be joined when the body member is expanded into contact with the vessel luminal walls.

15 Claims, 2 Drawing Sheets

26

24

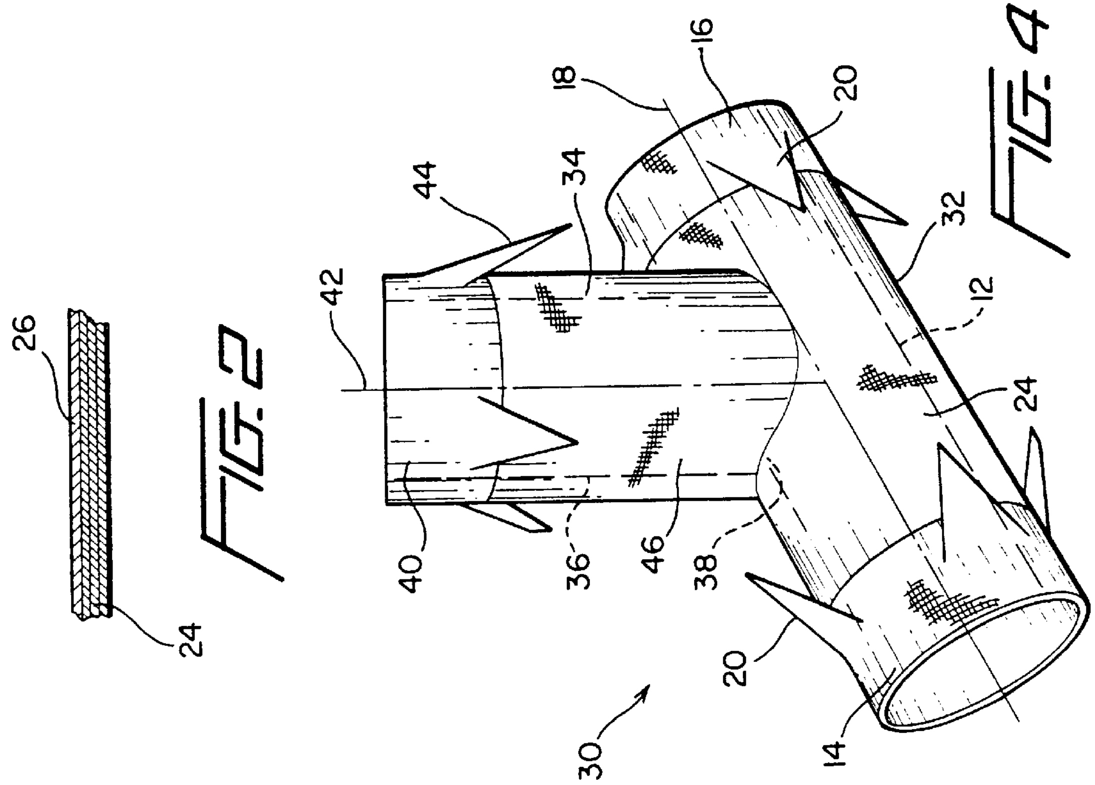
FIG. 2
FIG. 4
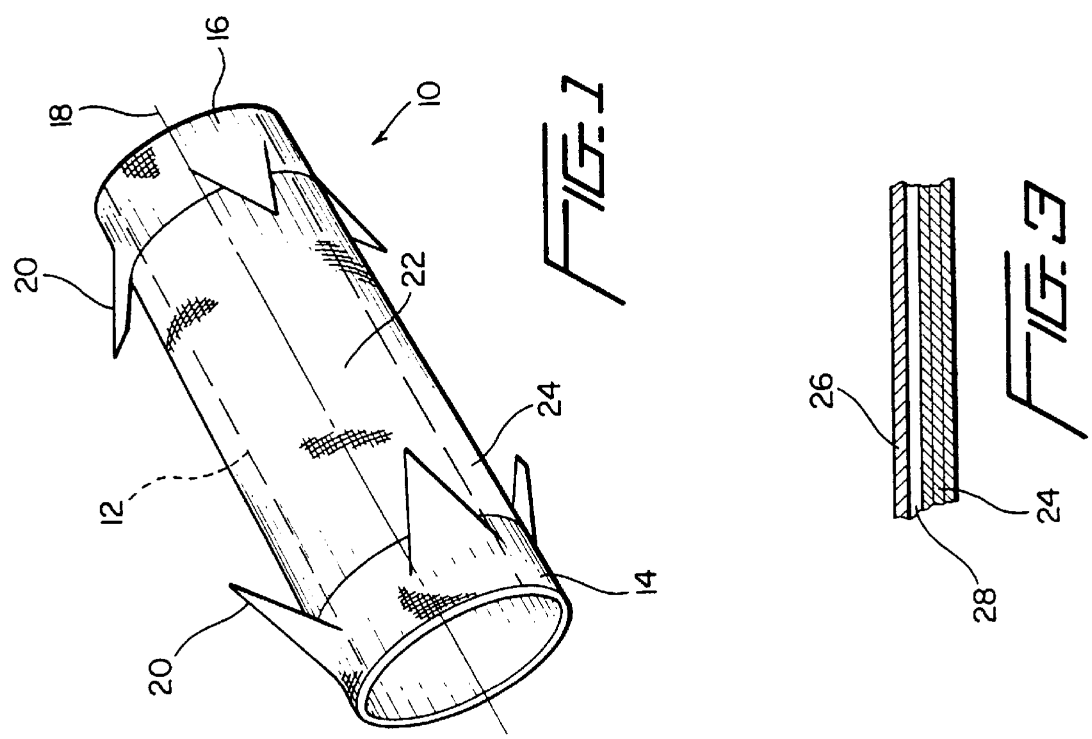
FIG. 1
FIG. 3

24
48
50
52
54
56
58
60
62
63
64
66
68
70
72
74
76
78
80

ANASTOMOSIS DEVICE

This application is a divisional application of U.S. Ser. No. 08/733,139 filed Oct. 16, 1996 now U.S. Pat. No. 5,755,778.

TECHNICAL FIELD

The present invention relates generally to devices for implementing a vascular graft and more particularly to an anastomosis device for use in performing a vascular graft without the necessity to employ sutures.

BACKGROUND OF THE INVENTION

In the past, sutures have been the primary means employed to connect blood vessels, ducts or other tubular body structures. Tubular body vessels are generally connected in end to end or end to side relationship and must be carefully sutured to prevent fluid leakage at the graft site. As surgical techniques and equipment used, for example in vascular surgery, have advanced, effective surgical procedures have been perfected which can be performed through very small incisions. However, as the size of the surgical incision required is minimized, it becomes an extremely difficult and time consuming operation to effectively suture two vessels together at a graft site.

Attempts have been made to position a stent inside a main blood vessel and to then use a separate graft device which is secured between the sidewall of a blood vessel and the stent. U.S. Pat. No. 5,456,712 to Maginot illustrates a two piece assembly of this type. The use of a separate graft unit in combination with a stent requires the ability to manipulate two separate units through a small incision, and a need exists for a unitary unit requiring only minimal manipulation to position and employ the unit to create an effective graft between two body vessels.

SUMMARY OF THE INVENTION

It is a primary object of the present invention to provide a novel and improved unitary anastomosis device for forming a tubular anastomosis while minimizing or eliminating the requirement for suturing.

Another object of the present invention is to provide a novel and improved anastomosis device which includes a tubular graft-like component formed of a body vessel compatible material carrying a bio-adhesive component which is activated to create a fluid leak tight seal with the luminal surface of a vessel.

Yet another object of the present invention is to provide a novel and improved anastomosis device having a reinforcing body portion combined with a tubular cover formed of body vessel compatible material. The reinforcing body portion is capable of assuming a first expanded configuration to bring the tubular cover into tight engagement with a vessel wall and a second contracted configuration to permit the reinforcing body portion and cover to fit within the small bore of a delivery catheter.

A further object of the present invention is to provide a novel and improved device for use within body vessels which includes a skeletal frame having an elongate, open ended main leg with a longitudinal axis extending between the open ends thereof, and at least one branch leg extending at an angle laterally from the main leg. The skeletal frame is adapted to assume a first expanded configuration to bring the main and branch legs into engagement with the luminal surfaces of the vessel walls for branched body vessels and a second contracted configuration to permit the skeletal frame to fit within the small bore of a delivery catheter.

Yet a further object of the present invention is to provide a novel and improved device for use within body vessels which includes a skeletal frame having an elongate open ended main leg with a longitudinal axis extending between the open ends thereof, and at least one branch leg extending at an angle laterally from the main leg. The branch leg includes a first end which opens into the main leg and an open end spaced therefrom with a branch leg longitudinal axis extending therebetween. The skeletal frame is formed by a plurality of interconnected cells with each cell having first and second spaced, substantially parallel cell sides which are joined to one of the first or second cell sides of an adjacent cell. The cell sides of the main leg are all substantially parallel to the longitudinal axis of the main leg while the cell sides of the branch leg are all substantially parallel to the branch leg longitudinal axis.

Another object of the present invention is to provide a novel and improved device for use within body vessels which includes a skeletal frame defining an elongate, open ended main leg with a longitudinal axis extending between the open ends thereof and at least one branch leg extending at an angle to the main leg longitudinal axis. The skeletal frame is adapted to assume a first expanded configuration to bring the main and branch legs into engagement with the luminal surfaces of the vessel walls for branched body vessels and a second contracted configuration to permit the skeletal frame to fit within the small bore of a delivery catheter. The skeletal frame is formed by a plurality of cells with each cell having first and second spaced, substantially parallel cell sides which are joined to one of the first or second cell sides of an adjacent cell. The cell sides of the main leg remain substantially parallel to the main leg longitudinal axis and the cell sides of the branch leg remain substantially parallel to the branch leg longitudinal axis in the first expanded configuration and the second contracted configuration of the skeletal frame as well as during the transition therebetween.

A still further object of the present invention is to provide a novel and improved anastomosis device having a reinforcing cellular frame formed of shape memory material which supports a collapsible cover of body vessel compatible material. The cover carries a bio-adhesive component which is activated to create a fluid leak tight seal when the frame expands to press the cover against the luminal surface of a body vessel.

BRIEF DESCRIPTION OF THE DRAWINGS

FIG. 1 is a perspective view of the anastomosis device of the present invention;

FIG. 2 is a sectional view of a portion of the fabric and adhesive coating for the anastomosis device of FIG. 1;

FIG. 3 is a sectional view of a portion of a second embodiment of the fabric and adhesive coating for the anastomosis device of FIG. 1;

FIG. 4 is a perspective view of a second embodiment of the anastomosis device of the present invention;

DESCRIPTION OF THE PREFERRED EMBODIMENTS

Figures 5, 6, 7:
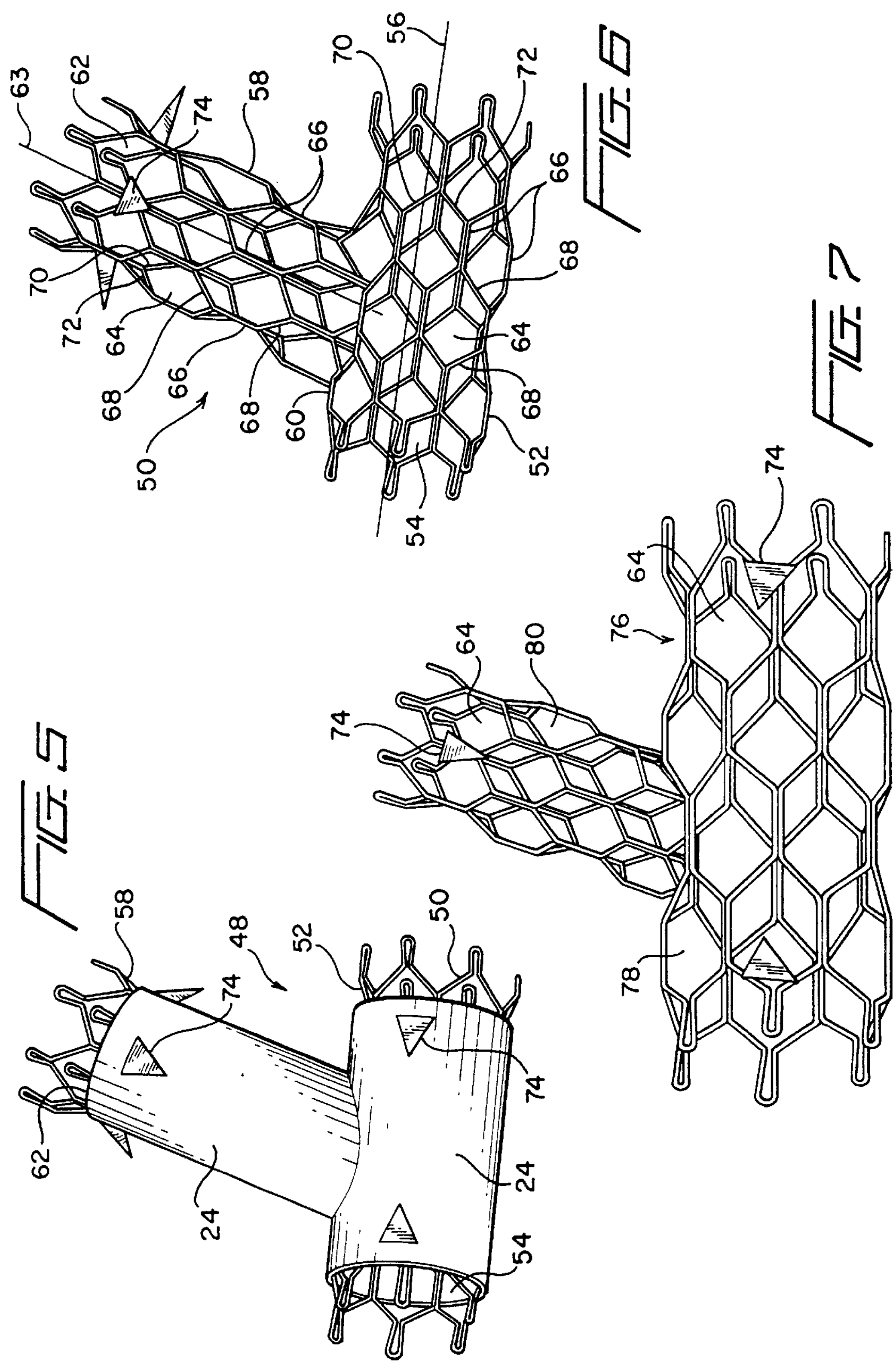
FIG. 5 is a perspective view of a third embodiment of the anastomosis device of the present invention.
FIG. 6 is a perspective view of a skeletal frame for engaging the luminal walls of two body vessels which may be employed with the anastomosis device of FIG. 5.
FIG. 7 is a perspective view of a second embodiment of a skeletal frame for engaging the luminal walls of two body vessels which may be employed with the anastomosis device of the present invention.

Referring now to the drawings, an anastomosis device indicated generally at 10 is provided for joining end to end two severed body vessels, such as blood vessels without the use of sutures. The anastomosis device 10 is tubular in configuration and defines an internal open ended channel 12 shown by broken lines in FIG. 1. At either end of the device are tubular collars 14 and 16 formed of expandable material so that the collars expand to the configuration shown in FIG. 1 but may be compressed toward a central longitudinal axis 18 for the internal channel 12. In the expanded condition, pointed barbs 20 project angularly and laterally outward from each of the collars 14 and 16. The barbs 20 extend angularly in opposite directions away from the respective ends of the anastomosis device toward the central portion thereof.

Secured to the collars 14 and 16 and extending therebetween is a fluid impervious, flexible tubular section 22 formed of a fabric like material 24 such as polytetrafluoroethylene (PTFE), urethane, elastomer or DACRON which is compatible with the body vessels to be joined by the anastomosis device. With reference to FIG. 2, the fabric 24 is impregnated with a bio-adhesive 26 which might be activated by contact with blood or other body fluid flowing through or in the area of the body vessels to be joined. This adhesive could be a gelatin-formaldehyde-resorcinol type glue or a photopolymerizing glue activated by light such as photoetheyleneglycol 400 diacrylate. In an alternative embodiment shown in FIG. 3, the fabric 24 carries both a microencapsulated adhesive activator 28 such as thrombin as well as a bio-adhesive 26 such as fibrin. When the tubular section 22 is expanded against a body vessel, pressure causes the rupture of the capsule containing the adhesive activator which then mixes with the bio-adhesive 26 to provide an adhesive bonding material over the surface of the tubular section 22.

In use, the anastomosis device 10 is compressed inwardly toward the longitudinal axis 18, and one end of a first body vessel is slipped over the collar 14 and is drawn over a portion of the tubular section 22. Then the end of a second body vessel is slipped over the collar 16 and drawn over another portion of the tubular section 24. The anastomosis device is permitted to expand within the two body vessels into contact with the luminal wall of each, and the barbs 20 engage the luminal walls to initially hold the vessels in place. This provides time for the bio-adhesive on the surface of the fabric 24 to bond with the luminal wall of each vessel creating a fluid tight seal therewith. The adhesive is either activated by bodily fluid, by some other means such as light, or is activated by rupture of the capsule for the adhesive activator 28.

The collars 14 and 16 are formed of material which is more rigid than the fabric 24 and the collars operate to expand the anastomosis device. These collars may be formed of expandable but flexible plastic, spring metal, or of a material which is expanded by an internal balloon such as that employed with a balloon catheter. Also, the collars 14 and 16 may be formed of a shape memory metal such as Nitinol which is pliable below a transition temperature level but which expands toward a predetermined shape when the transition temperature level is exceeded. The barbs 20 are normally formed of the same material as the collars 14 and 16.

For some applications, the anastomosis device can be expanded by an internal balloon which applies a positive pressure to the tubular section 22. This application of a positive pressure between the body vessels and the tubular section is advantageous when the microencapsulated adhesive activator is employed to assure that the adhesive activator is released. The use of the barbs 20 and the bio-adhesive 26 permit the anastomosis device 10 to securely join two body vessels end to end and to provide a fluid tight seal without the need for sutures. Tissue growth enhancers can also be provided on the surface of the tubular section 24 to support tissue growth of the two body vessels over the anastomosis device so that the two vessels grow together and insure hemosatosis.

With reference to FIG. 4, an anastomosis device 30 is illustrated which is operative to effectively join the end of a first body vessel to the side of a second body vessel without the use of sutures. This anastomosis device includes a main leg 32 which is substantially identical in structure to the anastomosis device 10, and structural units having the same structure and function as those in FIG. 1 are indicated by like reference numerals in FIG. 4.

Formed to be unitary with the main leg 32 and projecting angularly therefrom is a branch leg 34 which is tubular in configuration and which defines an internal channel 36 shown by broken lines in FIG. 4. The channel 36 has a first open end 38 which opens into the internal channel 12 and a second open end which is defined by a collar 40. The internal channel 36 includes a central longitudinal axis 42 which extends at an angle to the central longitudinal axis 18 of the main leg 32.

Like the collars 14 and 16, the collar 40 includes outwardly projecting barbs 44 which project angularly away from the open end of the collar. Extending from the collar 40 to the main leg 32 is a tubular section 46 formed of the fabric 24. The fabric of the tubular section 46 is joined to the fabric of the main leg 32 at a point between the collars 14 and 16, and the fabric of both the main leg and the branch leg is coated with the bio-adhesive structures of either FIGS. 2 or 3.

In use, the anastomosis device 30 is compressed within a delivery catheter and the delivery catheter is inserted into a first body vessel. An incision is made in the wall of the first body vessel and the anastomosis device 30 is positioned by the catheter so that when the catheter is withdrawn, the branch leg 34 projects outwardly through the incision. The barbs 20 for the collars 14 and 16 engage the luminal wall of the first body vessel in the manner previously described, and the bio-adhesive carried by the fabric 24 of the main leg 32 bonds to the luminal wall of the first body vessel. In the meantime, the second body vessel is inserted over the collar 40 and drawn down over the branch leg 34. The barbs 44 of the collar 40 engage the luminal wall of this second body vessel to hold it in place until the bioadhesive carried by the fabric of the tubular section 46 bonds to the luminal wall of the second body vessel.

The collar 40 for the branch leg 34 is normally formed of the same material which forms the collars 14 and 16. However, it is possible to form the collars 14 and 16 of plastic or spring metal which expand the collars outwardly when the catheter is removed, while the collar 40 could be formed of a thermal shape memory material having a thermal transition temperature such that the collar does not expand until it is inserted within the second body vessel and is warmed by body temperature. Conversely, the collars 14 and 16 may also be formed of a thermal shape memory material which expands within the first body vessel when the catheter is removed, and the collar 40 would then expand when it is inserted within the second body vessel to be warmed by body temperature.

It is sometimes desirable to ensure that the main and branch legs of an anastomosis device are supported with greater rigidity and expand into positive contact with two vessels over the entire length of the main and branch legs. Referring to FIGS. 5 and 6, an anastomosis device 48 capable of providing these support and expansion characteristics is illustrated. The anastomosis device 48 includes a skeletal frame 50 having a main leg 52 which is tubular in configuration and is formed to define an elongated, open ended main chamber 54 having a central longitudinal axis 56. The skeletal frame 50 also includes a branch leg 58 which is connected at one end 60 to the main leg 52 and which extends angularly outward therefrom. The branch leg 58 is also tubular in configuration and defines an elongate branch chamber 62 having a central longitudinal axis 63 which extends at an angle to the longitudinal axis 56. One end of the branch chamber 62 opens at 60 into the main chamber 54, while the opposite end of the branch chamber is open.

The skeletal frame 50 is shown in the expanded configuration thereof in FIGS. 5 and 6 and is preferably formed of wire or a similar elongate strand or strands of material configured to provide a mesh comprising a plurality of interconnected open cells 64 which form the main and branch legs of the skeletal frame. The cells 64 are preferably of a polygonal configuration when viewed in plan. It is important to note that each cell is formed by two spaced straight side portions or walls 66 which are substantially parallel to the central longitudinal axis of either the main chamber or branch chamber in the leg of the skeletal frame of which the cell is a part. Each end of a cell is closed by an end wall 68 which extends at a angle to the longitudinal axis of either the main chamber or the branch chamber depending upon whether the cell is in the branch leg or the main leg of the skeletal frame. Preferably, the end walls of each cell are formed by two inclined end sections 70 and 72 which incline outwardly from the straight side portions 66 of the cell and meet at an apex centrally of the cell.

The cells are connected together only along abutting straight elongate side portions 66, preferably by welding, and the end walls 68 remain unconnected. Preferably the cells 64 are polygonal and there are six cells in each circumferential row around the main and branch legs of the skeletal frame.

The skeletal frame 50 is designed to be collapsed within a delivery catheter, and to collapse the skeletal frame, the inclined cell end walls 70 and 72 permit the straight elongate side portions of the cell to be moved together to compress the leg containing the cell toward the central longitudinal axis of the chamber through the leg. As each cell collapses from the expanded configuration shown in FIG. 6 to a collapsed configuration, the straight elongate side portions 66 of the cell are maintained parallel to the respective chamber longitudinal axis. Thus, as the cells of the main leg 52 of the skeletal frame 50 move between the expanded configuration and the collapsed configuration, they are maintained substantially parallel to the central longitudinal axis 56, while the cells of the branch leg 58 are maintained substantially parallel to the longitudinal axis 63 as they move between the expanded configuration and the contracted configuration. Once the cells in the main and branch legs of the skeletal frame have been moved to the contracted configuration, the branch leg may be flexed downwardly against the main leg to permit the complete device to be fit within the bore of a catheter.

As illustrated by FIG. 5, the main leg 52 and the branch leg 58 of the skeletal frame 50 are covered by the fabric 24 bearing the bio-adhesive of either FIG. 2 or FIG. 3. It is possible to provide the skeletal frame 50 with inclined laterally projecting barbs 74 which project through the fabric 24. For many uses, however, the barbs can be completely eliminated since the combination of the force provided by the skeletal frame 50 and the bonding effect of the bio-adhesive 26 will hold the anastomosis device in place and create an effective fluid seal with the luminal walls of two body vessels.

The skeletal frame 50 may be formed of spring metal, plastic, or similar material which will expand to the configuration shown in FIG. 6, but preferably, the skeletal frame is formed of a thermal shape memory material such as Nitinol. The unique characteristic of a thermal shape memory material is its response to a temperature transformation level below which the material becomes quite pliable, collapsible and compressible. Above the temperature transformation level, the material becomes relatively rigid though somewhat flexible and returns to its expanded memory shape with the cell configuration of FIG. 6. The inclined end sections 70 and 72 change condition as the skeletal frame is subjected to temperatures above and below the transition temperature to move the straight side portions of the cell together or apart.

In the anastomosis device 48 of FIG. 5, the material 24 may be an elastomeric material which expands as the skeletal frame expands but which applies pressure to the skeletal frame in the expanded condition thereof so that as the frame passes below the transition temperature, the action of the elastomeric cover moves the frame to the compressed configuration. It is possible to make the temperature transition level of the main leg 52 of the skeletal frame different from the temperature transition level of the branch leg 58 by, for example, varying the alloy composition of the material forming the main and branch legs or by varying the annealing temperatures of the main and branch legs which are used to set the respective transition temperatures.

As shown by FIG. 7, a skeletal frame 76 can be provided with a main leg 78 which will expand outwardly for a greater distance than will the branch leg 80. This will cause the main leg to either fit within a larger vessel, or to provide a greater pressure against the luminal walls of a main vessel that is the same diameter as a branch vessel applied to the branch leg 80. This greater expansion characteristic is provided by making the cells 64 of the main leg larger than the cells 64 of the branch leg.

INDUSTRIAL APPLICABILITY

The anastomosis device of the present invention is a unitary unit which may easily be positioned and used to join two body vessels without the need for suturing. The device employs automatically activated bio-adhesives which bind the device to the luminal walls of two tubular body vessels to create a fluid tight graft.

I claim:

1. The anastomosis device for use in forming a graft between at least two body vessels comprising:

a body member for engaging the luminal walls of said body vessels formed to define a main leg with an elongate main chamber having at least first and second spaced open ends and a central longitudinal axis extending between said first and second open ends, said body member including a first tubular collar defining said first open end of said body member, a second tubular collar defining said second open end of said body member, said first and second collars being formed of thermal shape memory material having a temperature transformation level wherein at a temperature above which said first and second collars assume a first predetermined expanded configuration and become relatively rigid, and wherein at a temperature below which said first and second collars become pliable and are collapsible inwardly toward said central longitudinal axis to a second collapsed configuration, and a first flexible tubular section formed of flexible, fluid impervious, body vessel compatible material extending between said first and second collars, said first flexible tubular section having a first end connected to said first collar and a second end connected to said second collar to form therewith said elongate main chamber, said first and second collars being operative in said first expanded configuration to each contact the luminal wall of a body vessel, said first and second collars being made of a material more rigid than said first flexible tubular section material in the expanded configuration of said first and second collars to form a body member with relatively rigid ends joined by the first flexible tubular section, and a unitary branch leg secured to and extending angularly outward from said main leg between said first and second collars, said branch leg including a third tubular collar defining an open end of said branch leg and a second flexible tubular section having an outer end secured to said third collar and an inner end secured to said first flexible tubular section and opening into said first flexible tubular section, said second flexible tubular section being formed of flexible, fluid impervious, body vessel compatible, material and with said third collar defining an elongate, open ended branch chamber with an end opening into said main chamber, said third collar being formed of thermal shape memory material having a temperature transformation level wherein at a temperature above which said third collar assumes a third predetermined expanded configuration and becomes relatively rigid, and at a temperature below which said third collar becomes pliable and collapsible inwardly to a fourth collapsed configuration, said third collar being operative in said third expanded configuration to contact the luminal wall of a second body vessel, said third collar being made of material more rigid than said second flexible tubular section material in the third expanded configuration to form a body member with three relatively rigid ends joined by the first and second flexible tubular sections when said first and second tubular collars are in the first expanded configuration and said third tubular collar is in the third expanded configuration.

2. An anastomosis device for use in forming a graft between at least two body vessels comprising:

a body member for engaging the luminal walls of said body vessels formed to define at least one elongate main chamber having at least first and second spaced open ends and a central longitudinal axis extending between said first and second open ends, said body member including a first tubular collar defining said first open end of said body member, a second tubular collar defining said second open end of said body member, and a tubular section formed of flexible, fluid impervious, body vessel compatible material having a first end connected to said first collar and a second end connected to said second collar, said first and second collars being operative to assume a first expanded configuration to each contact the luminal wall of a body vessel and a second collapsed configuration inwardly toward said central longitudinal axis, said first and second collars being more rigid than said flexible section in the expanded configuration, said first and second collars forming a main leg, said body member further including a branch leg secured to and extending angularly outward from said main leg, said branch leg including a third collar defining an open end of said branch leg and a second tubular section having an outer end secured to said third collar and an inner end secured to said first tubular section and opening into said first tubular section, said second tubular section being formed of flexible, fluid impervious, body vessel compatible material and with said third collar, defining an elongate, open ended branch chamber with an end opening into said main chamber, said third collar being operative to assume a first expanded configuration to contact the luminal wall of a body vessel and a second collapsed configuration inwardly of said first expanded configuration, said first, second and third collars being formed of thermal shape memory material having a temperature transformation level above which the collar assumes said first expanded configuration and below which the collar is collapsible to said second collapsed configuration, the temperature transformation level of said third collar being different from the temperature transformation level of said first and second collars.

3. A device adapted to engage the luminal walls of a main body vessel and a branch body vessel extending from said main body vessel comprising:

a skeletal frame formed of thermal shape memory material having at least one temperature transformation level above which said skeletal frame assumes a first expanded configuration and becomes relatively rigid and below which said skeletal frame becomes pliable and is collapsed to a second collapsed configuration, said skeletal frame having an elongate main leg formed to define an elongate, open ended main chamber and a branch leg connected to and extending angularly from said main leg and formed to define a branch chamber having a first open end opening into said main chamber and a second open end spaced therefrom, the main chamber having a central longitudinal axis extending between the open ends thereof and the branch chamber having a central longitudinal axis extending between the first and second ends thereof at an angle to the longitudinal axis of the main chamber, said main leg being formed to define a plurality of interconnected open cells, each of said cells including two substantially parallel straight side portions which are substantially parallel to the central longitudinal axis of said main chamber and end walls extending between said straight side portions at an angle to the central longitudinal axis of said main chamber and said branch leg being formed to define a plurality of interconnected open cells, each of said cells including two substantially parallel straight side portions which are substantially parallel to the central longitudinal axis of said branch chamber and end wall means extending between said straight side portions at an angle to the central longitudinal axis of said branch chamber the interconnected open cells of one of said main or branch legs being larger than the interconnected open cells of the remaining legs.

4. A device adapted to engage the luminal walls of a main body vessel and a branch body vessel extending from said main body vessel comprising:

a skeletal frame having an elongate main leg formed to define an elongate, open ended main chamber and a branch leg connected to and extending angularly from said main leg and formed to define a branch chamber having a first open end opening into said main chamber and a second open end spaced therefrom, the main chamber having a central longitudinal axis extending between the open ends thereof and the branch chamber having a central longitudinal axis extending between the first and second ends thereof at an angle to the longitudinal axis of the main chamber, said main leg being formed to define a plurality of interconnected open cells, each of said cells including two substantially parallel straight side portions which are substantially parallel to the central longitudinal axis of said main chamber and end walls extending between said straight side portions at an angle to the central longitudinal axis of said main chamber and said branch leg being formed to define a plurality of interconnected open cells, each of said cells including two substantially parallel straight side portions which are substantially parallel to the central longitudinal axis of said branch chamber and end wall means extending between said straight side portions at an angle to the central longitudinal axis of said branch chamber, the interconnected open cells of said main leg being larger than the interconnected open cells of said branch leg.

5. A device adapted to engage the luminal walls of a main body vessel and a branch body vessel extending from said main body vessel comprising:

a skeletal frame having an elongate main leg formed to define an elongate, open ended main chamber and a branch leg connected to and extending angularly from said main leg and formed to define a branch chamber having a first open end opening into said main chamber and a second open end spaced therefrom, the main chamber having a central longitudinal axis extending between the open ends thereof and the branch chamber having a central longitudinal axis extending between the first and second ends thereof at an angle to the longitudinal axis of the main chamber, said main leg being formed to define a plurality of interconnected open cells, each of said cells including two substantially parallel straight side portions which are substantially parallel to the central longitudinal axis of said main chamber and end walls extending between said straight side portions at an angle to the central longitudinal axis of said main chamber and said branch leg being formed to define a plurality of interconnected open cells, each of said cells including two substantially parallel straight side portions which are substantially parallel to the central longitudinal axis of said branch chamber and end wall means extending between said straight side portions at an angle to the central longitudinal axis of said branch chamber, the cells of said main leg being joined together only along the straight side portions thereof and the cells of said branch leg being joined together only along the straight side portions thereof, said skeletal frame being operative to assume a first expanded configuration to cause said main and branch legs to engage the luminal walls of said body vessels and a second collapsed configuration to collapse said main and branch legs toward and adjacent to the longitudinal central axes of the main and branch chambers respectively, the end wall means of each cell in said main and branch legs operating to cause the space between the straight side portions of the cell to increase to expand the skeletal frame from said second collapsed configuration to said first expanded configuration and to cause the space between the straight side portions of the cell to decrease in order to collapse the skeletal frame from said first expanded configuration to said second collapsed configuration, the skeletal frame being formed of shape memory material having at least one temperature transformation level above which said skeletal frame assumes said first expanded configuration and below which said skeletal frame is collapsible to said second collapsed configuration, the temperature transformation level of the skeletal frame in said main leg being different from the temperature transformation level in the branch leg of said skeletal frame.

6. The anastomosis device for use in forming a graft between at least two body vessels comprising:

a body member for engaging the luminal walls of said body vessels formed to define a main leg with an elongate main chamber having at least first and second spaced open ends and a central longitudinal axis extending between said first and second open ends, said body member including a first tubular collar defining said first open end of said body member, a second tubular collar defining said second open end of said body member, said first and second collars being formed of thermal shape memory material having a temperature transformation level wherein at a temperature above which said first and second collars assume a first predetermined expanded configuration and become relatively rigid, and wherein at a temperature below which said first and second collars become pliable and are collapsible inwardly toward said central longitudinal axis to a second collapsed configuration, and a first flexible tubular section formed of flexible, fluid impervious, body vessel compatible material extending between said first and second collars, said flexible tubular section having a first end connected to said first collar and a second end connected to said second collar to form therewith said elongate main chamber, said first and second collars being operative in said first expanded configuration to each contact the luminal wall of a body vessel, said first and second collars being more rigid than said first flexible tubular section in the expanded configuration of said first and second collars to form a body member with relatively rigid ends joined by the first flexible tubular section, said body member including an outer surface and a bio-adhesive and an encapsulated bio-adhesive activator are carried on said outer surface.

7. A device adapted to engage the luminal walls of a main body vessel and a branch body vessel extending from said main body vessel comprising:

a skeletal frame having an elongate main leg formed of a plurality of interconnected open cells and configured to define an elongate, open ended main chamber and a branch leg connected to and extending angularly from said main leg and formed of a plurality of interconnected open cells and configured to define a branch chamber having a first open end opening into said main chamber and a second open end spaced therefrom, the main chamber having a central longitudinal axis extending between the open ends thereof and the branch chamber having a central longitudinal axis extending between the first and second ends thereof at an angle to the longitudinal axis of the main chamber, said skeletal frame being formed of shape memory material which is operative above a temperature transformation level to assume a first expanded configuration and below said temperature transformation level to assume a second collapsed configuration where said main and branch legs are collapsed toward the respective longitudinal axes thereof, the temperature transformation level of the skeletal frame in said main leg being different from the temperature transformation level in the branch leg of said skeletal frame.

8. The device of claim 3 wherein the leg of said main or branch legs having the larger interconnected open cells defines an open ended chamber having a greater cross sectional area than the cross sectional area defined by the interconnected open cells of the remaining leg.

9. The anastomosis device of claim 7 wherein said body member includes an outer surface and a tissue growth enhancer is carried by said outer surface.

10. The anastomosis device of claim 1 wherein said body member includes laterally projecting barbs formed on said first, second and third collars for penetrating the luminal wall of a body vessel when said first, second and third collars are in the first and third expanded configurations.

11. The device of claim 8 wherein the cells of said main leg are joined together only along the straight side portions thereof and the cells of said branch leg are joined together only along the straight side portions thereof.

12. The device of claim 11 wherein said skeletal frame is operative to assume a first expanded configuration to cause said main and branch legs to engage the luminal walls of said body vessels and a second collapsed configuration to collapse said main and branch legs toward and adjacent to the longitudinal central axes of the main and branch chambers respectively, the end wall means of each cell in said main and branch legs operating to cause the space between the straight side portions of the cell to increase to expand the skeletal frame from said second collapsed configuration to said first expanded configuration and to cause the space between the straight side portions of the cell to decrease in order to collapse the skeletal frame from said first expanded configuration to said second collapsed configuration.

13. The device of claim 12 wherein the end wall means of the cells in said main leg maintain the straight side portions thereof substantially parallel to the central longitudinal axis of said main chamber in said first expanded configuration and said second collapsed configuration and during the transition therebetween and the end wall means of the cells in said branch leg maintain the straight side portions thereof substantially parallel to the central longitudinal axis of said branch chamber in said first expanded configuration and said second collapsed configuration and during the transition therebetween.

14. The device of claim 13 wherein said cell end wall means each include first and second wall sections, each said wall section having a first end joined to one of the side portions of said cell, said wall section extending at an angle to the side portion to which the first end thereof is joined, and each said wall section having a second end opposite to said first end, the second ends of said first and second wall sections being joined.

15. The anastomosis device of claim 1 wherein said body member includes an outer surface and a bio-adhesive is carried by said outer surface.

* * * * *